United States Patent [19]

Chan et al.

[11] Patent Number: 5,886,182
[45] Date of Patent: Mar. 23, 1999

[54] CHIRAL PYRIDYLPHOSPHINES AND THEIR APPLICATION IN ASYMMETRIC CATALYTIC HYDROGENATION OF 2-ARYLPROPENOIC ACIDS

[75] Inventors: Albert Sun-Chi Chan; Cheng-Chao Pai, both of Kowloon, Hong Kong

[73] Assignee: The Hong Kong Polytechnic University, Kowloon, Hong Kong

[21] Appl. No.: 988,376

[22] Filed: Dec. 10, 1997

[51] Int. Cl.$^6$ ........................................................... C07F 9/50
[52] U.S. Cl. ........................................................... 546/21
[58] Field of Search ................................. 546/21; 568/16

[56] References Cited

U.S. PATENT DOCUMENTS

| | | | |
|---|---|---|---|
| 5,144,050 | 9/1992 | Chan et al. | 556/20 |
| 5,508,438 | 4/1996 | Broger | 549/6 |
| 5,516,944 | 5/1996 | Broger | 568/13 |
| 5,621,128 | 4/1997 | Jendralla | 556/18 |
| 5,710,339 | 1/1998 | Laue | 568/16 |
| 5,789,592 | 8/1998 | Gratzel | 546/21 |

OTHER PUBLICATIONS

Chan, A.S.C., et al, "Synthesis of 2,2'–Bis(diphenylphosphino) . . . Acrylic Acids", J. Am. Chem. Soc., V. 102, pp. 7932–7934, 1980.

Schmid, R., et al, "102.Axially Dissymmetric . . . of N,N–Diethylnerylamine", Helvetica Chimica Acta, V. 71, pp. 897–929, 1988.

Miyashita, A., et al, "Synthesis of Atropisomeric . . . Hydrogenation of Prochiral Olefins", Chemistry Letters, pp. 1849–1852, 1989.

Schmid, R. et al, "35.Axially Dissymmetric Diphosphines in the . . . Approach", Helvetica Chimica Acta, V. 74, pp. 370–389, 1991.

Cai, D., et al, "Synthesis of Chiral 2,2'Bis(diphenylphosphino) . . . Insertion", J. Org. Chem., V. 59, pp. 7180–7181, 1994.

Kumobayashi, H., et al, "Recent Advances in Chiral Catalysis", Chiral Tech 96, 14 pages, 1996.

Ohta, T., et al, "Asymmetric Hydrogenation of Unsaturated . . . Complexes", J. Org. Chem., V. 52, pp. 3174–3176, 1987.

Khanapure, S.P., et al, "A Convenient Synthesis of . . . 3–Cyano–1–(3HO–Isobenzofuranones", Heterocycles, V. 27, pp. 2643–2651, 1988.

CA:121:255383 abs J Fluorine Chem 68(2) pp. 131–134, 1994.

CA:66:66032 abs of US3298967, Jan. 1967.

CA:1211299 abs of "Chemistry of heterocyclic compounds. 27 An improved preparation of pyridyldiphenylphosphines", J Org Chem, 43(5), pp. 947–949, 1978.

*Primary Examiner*—Gary Geist
*Assistant Examiner*—Jean F Vollano
*Attorney, Agent, or Firm*—Leydig, Voit & Mayer

[57] ABSTRACT

Novel, optically active phosphorous compounds of the formula,

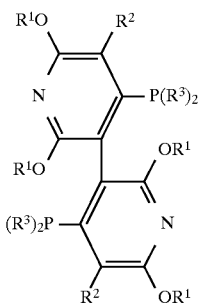

wherein $R^1$ represents hydrogen atoms, straight or branched-chain alkyl groups having from 1 to 6 carbon atoms, $R^2$ represents hydrogen atoms, halogen atoms, lower alkyl groups (1 to 6 carbon atoms), lower alkoxy groups (1 to 6 carbon atoms), hydroxy group, chiral hydroxyalkyl groups, and amino groups (1°, 2°, 3°) vinyl groups or allyl groups and $R^3$ represents phenyl groups, aryl groups, cyclohexyl groups, substituted and unsubstituted cycloalkyl groups, heteroaromatic rings, are described. The compounds of the formula serve as highly useful ligands in the preparation of ruthenium complexes which are effective catalysts for the asymmetric hydrogenation of 2-arylpropenoic acids leading to high valued 2-arylpropionic acids.

6 Claims, No Drawings

CHIRAL PYRIDYLPHOSPHINES AND THEIR APPLICATION IN ASYMMETRIC CATALYTIC HYDROGENATION OF 2-ARYLPROPENOIC ACIDS

BACKGROUND OF THE INVENTION

1. Field of the Invention

This invention relates to a new class of novel organic atropisomeric diphosphine compounds 2,2',6,6'-tetraalkoxy-4,4'-bis(disubstituted-phosphino)-5,5'-disubstituted-3,3'-bipyridine or 2,2',6,6'-tetraalkoxy-4,4'-bis(disubstituted-phosphino)-3,3'-bipyridine compounds {(R)- or (S)-form} and the preparation of these compounds. This invention also relates to the asymmetric catalytic hydrogenation of 2-arylpropenoic acids to give the corresponding 2-arylpropionic acids in high enantiomeric excess. More particularly, the present invention relates to the creation of a class of highly effective chiral catalysts which can be easily recycled through phase-separation from the products. The improved asymmetric catalytic hydrogenation process of the present invention is particularly suitable for use in the synthesis of 2-(6'-methoxy-2'-naphthyl)propionic acid (naproxen) and 2-(p-isobutylphenyl)propionic acid [(S)-ibuprofen].

2. Prior Art

Atropisomeric diphosphines such as BINAP (J. Am. Chem. Soc. 1980, 102, 7932) [2,2'-bis(diphenylphosphino)-1,1'-binaphthyl] and its derivatives have found widespread use in metal-catalyzed asymmetric catalytic reactions.

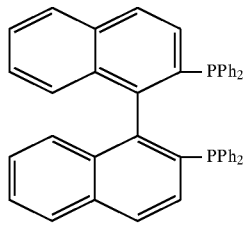

BINAP

In particular, BINAP type diphosphines are most useful ligands for enantioselective hydrogenation reactions. Considerable efforts have been undertaken for the design and synthesis of other atropisomeric diphosphine ligands in biphenyl series, for example BIPHEMP (Eur. Pat. No. 104375, 1983); Helv. Chim. Acta. 1988, 71, 897), BICHEP (Chem. Lett. 1989,1849) and MeOBIPHEP (Helv. Chim. Acta. 1991, 74, 370).

The synthesis of BINAP type ligands is difficult. The traditional method requires high temperature (~340° C.) and corrosive conditions to convert 2,2'-dihydroxy-1,1'-binaphthene to the key intermediate 2,2'-dibromo-1,1'-binaphthene for the synthesis of BINAP. Scientists at Merck (J. Org. Chem. 1994, 59, 7180) and Takasago (Chiral Tech 1996 ) reported the synthesis of BINAP by using nickel or palladium catalyzed coupling reaction of 2,2'-bis[(trifluoromethanesulfonyl)oxy]-1,1'-binaphthyl with diphenylphosphine or diphenylphosphine oxide. This approach requires the expensive trifluoromethanesulfonic anhydride and several extra steps for the synthesis of BINAP, MeOBIPHEP, BIPHEMP and BICHEP. The separation of the homogeneous catalysts from the reaction products is also difficult, making the recycling of the expensive catalysts complicated and consequently the commerical application of these ligands quite expensive.

Naproxen is a nonsteroidal drug with anti-inflammatroy, analgesic and antipyretic activities. It belongs to a group of compounds generally classified as arylpropionic acids or arylalkanoic acids. Many synthetic routes for producing optically pure arypropionic acids have been proposed. These methods include the resolution of a mixture of enantiomers by using a resolving agent such as cinchonidine or glucamine. These resolution procedures require numerous recrystallizations. U.S. Pat. No. 4,542,237 discloses a process for preparing 2-arylpropionic acids and, in particular, a process for preparing naproxen, involving a non-catalytic process which is, therefore, not commerically attractive. The asymmetric hydrogenation of arylpropenoic acid has been previously proposed as a method of producing optically active 2-arylpropionic acids. For example, Campoli et al., U.S. Pat. No. 4,239,914 described catalytic asymmetric hydrogenation of 2-(6-methoxy-2-naphthyl)acrylic acid utilizing a rhodium catalyst containing a chiral bidentate phosphine ligand, e.g. DIPAMP, DIOP or PNNP but the enantiomeric excess of the desired product was reported to be only around 70% or less.

Noyori et al., reported the asymmetric hydrogenation of 2-(6'-methoxy-2'-naphthyl)propenoic acid with a catalytic amount of Ru[(S)-BINAP](OAc)$_2$ at about 13800 KPa H$_2$ to give naproxen in J. Org. Chem. 1987, 52,3174–3176.

Chan et al., also reported the asymmetric catalytic hydrogenation of 2-arylpropenic acids with Ru-BINAP type catalysts to produce naproxen in U.S. Pat. No. 4,994,607 and U.S. Pat. No. 5,144,050.

For the economical production of naproxen, S-ibuprofen and other similar products, it is highly desirable to invent a new class of catalysts which are more effective than Ru(BINAP) and are easily separated from the reaction products.

SUMMARY OF THE INVENTION

The present invention provides a new class of highly useful atropisomeric diphosphines, namely (R)- or (S)-form 2,2',6,6'-tetraalkoxy-4,4'-bis(disubstituted-phosphino)-5,5'-disubstituted-3,3'-bipyridine or 2,2',6,6'-tetraalkoxy-4,4'-bis(disubstituted-phosphino)-3,3'-bipyridine and convenient methods for the synthesis of them and their Ru(II) complexes. This invention also relates to the use of the new Ru catalysts in the asymmetric catalytic hydrogenation of 2-arylpropenoic acids to give the corresponding 2-arylpropionic acids in higher enantiomeric excess than that with the well known Ru(BINAP) catalyst systems under similar reaction conditions. The new catalysts also have the advantage of being easily separated from the organic product via phase separation.

DETAILED DESCRIPTION OF THE INVENTION

The present invention is concerned with a class of novel, optically active phosphorous compounds of the general formula (1) and the synthetic routes of these ligands as follow. The structure of compound of formula (1) is shown below:

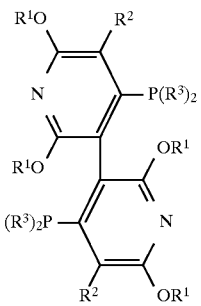
(1)

wherein:

(a) $R^1$ is chosen from the group comprising hydrogen atoms and straight or branched chain alkyl groups having from 1 to 6 carbon atoms;

(b) $R^2$ is chosen from the group comprising hydrogen atom, halogen atoms, lower alkyl groups (1 to 6 carbon atoms), lower alkoxy groups (1 to 6 carbon atoms), hydroxy group, chiral alcohol groups, amino groups (1°,2°,3°), vinyl groups and allyl groups; and (c) $R^3$ is chosen from the group comprising:

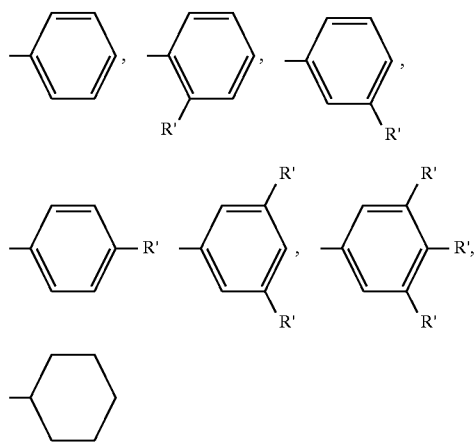

in which R' represents a straight or branched chain alkyl group having from 1 to 6 carbon atoms, an alkoxy group having from 1 to 6 carbon atoms, or an amino group and, where there is more than one group R', each may be the same or different from the others; or the group $P(R^3)_2$ may form a group chosen from the following structures:

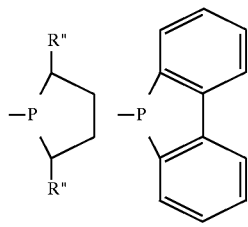

in which R" is a straight or branched chain alkyl group having from 1 to 6 carbon atoms.

A related intermediate, compound (2), is useful for the preparation of the key precursor to (1). The structure of (2) is shown below:

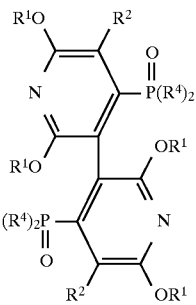
(2)

wherein $R^1$ and $R^2$ are as defined above, and $R^4$ represents a lower alkoxy group, phenoxy group, benzyloxy group or a chlorine or bromine atom. When $R^4$ represents halogen atom, compound (2) can react with a compound of the formula $R^3MgX$ or $R^3Li$ wherein $R^3$ is as defined above and X represents a chlorine, bromine or iodine atom, to give a compound of the formula (3).

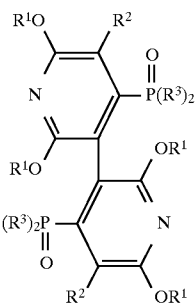
(3)

wherein $R^1$, $R^2$ and $R^3$ are as defined above. Compound (3) can be reduced to compound (1) after separation into the R-form and S-form using chiral HPLC column (for example, Diacel AD column) or via chemical resolution.

The reduction of the R- or S-form compound of formula (3) can be carried out in a known manner. This can be effected, for example, with a silane such as trichlorosilane in an aromatic hydrocarbon solvent such as xylene or toluene in the presence of an auxiliary base such as tributylamine or triethylamine. Similar reduction has been used by Noyori et al., (J. Am. Chem. Soc. 1980,102, 7932) for the preparation of BINAP from BINAPO.

The compounds of formula (2) which are used as a starting material can be prepared, for example, from a compound of the formula (4) or (5):

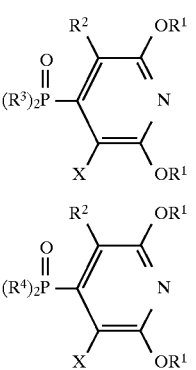

wherein $R^1$, $R^2$, $R^3$ and $R^4$ are as defined above, via Ullmann coupling (Synthesis 1974, 9), to obtain products of formula (2) and (3). This Ullmann coupling reaction can be carried out, for example, by heating a compound of formula (4) or (5) in an inert organic solvent such as N,N'-dimethylformamide with copper powder activated with iodine to a temperature of about 110° C. to 200° C.

The compounds of general formula (4) and (5), which are used as starting materials, can be prepared from a compound of the general formula (6):

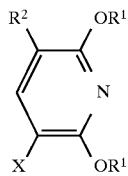
(6)

wherein $R^1$, $R^2$ and X are as defined above. Preferably, $R^2$ may be a chlorine, bromine or iodine atom. In a typical preparative procedure compound (6) is deprotonated with a base such as lithium diisopropylamide at low temperature and the deprotonated intermediate is allowed to react with $ClP(R^3)_2$ or $ClP(R^4)_2$ wherein $R^3$ and $R^4$ are as defined above to give a compound of the formula (4) or (5). Compound (6), where the $R^2$ represents a chlorine, bromine or iodine atom or hydrogen atom, can be prepared according to a method reported in the literature (*Heterocycles* 1988, 27, 11.).

For the purpose of this invention, the catalysts can be prepared by the reaction of diphosphines with Ru(COD)(OAc)$_2$ (*J. Org. Chem.* 1987,52,3174), [Ru(cymene)X$_2$]$_2$ (*J. Org. Chem.* 1994,59, 3064) or Ru(acac)$_3$(U.S. Pat. No. 5,144,050, 1992) (in the presence of a reducing agent such as zinc dust in the latter case), wherein COD represents a cyclooctadiene group, OAc represents an acetoxy group, X represents a halogen atom and acac represents an acetylacetonate group in a suitable organic solvent such as methanol or ethanol, to produce the ruthenium complexes.

For the purpose of this invention, the ruthenium complexes can be used as catalysts in the hydrogenation of 2-arylpropenoic acids. Enantiomeric excesses were determined by chiral HPLC utilizing a SUMICHIRAL OA-2500 column. In the following examples, the following abbreviations are used: LDA=lithium diisopropylamide; THF=tetrahydrofuran; DMF=N,N'-dimethylformamide; (PP)=(R)-2,2,6,6'-tetramethoxy-4,4'-diphenylphosphino-3,3'-bipyridine; acac=acetylacetonate; HPLC=high pressure liquid chromatography; sub.=2-(6'-methoxy-2'-naphthyl) propenoic acid.

EXAMPLE 1

Preparation of 2,6-dimethoxy-3-bromo-4-(diphenylphosphino)pyridine

To a magnetically stirred solution of 4.0 mL of approximatly 2.0M LDA solution (in hexane) (7.98 mmol) was added a solution of 2,6-dimethoxyl-3-bromopyridine (3.14 g, 6.14 mmol) in 10 mL of THF at −78° C. over a period 20 minutes while the internal temperature was kept below −78° C. To the resulting red-brown suspension was added a solution of chlorodiphenylphosphine (1.20 mL, 6.75 mmol) in the 10 mL of THF at −78° C. The reaction mixture was allowed to warm to ambient temperature overnight and was poured into 20 mL water. The organic product was extracted with dichloromethane (3×20 mL). The combined extract was dried with anhydrous magnesium sulfate and was concentrated in vaccuo to give a crude product which was recrystallized in methanol to give 2.34 g of pure product (95% theoretical yield).

$^1$H-NMR(400 MHz): δ 3.83 (s, 3H, OCH$_3$), 4.00 (s, 3H, OCH$_3$), 5.71 (d, J$_{PH}$=2.4 Hz, 1H, PyH's), 7.38~7.28 (m, 10H, PhH's).

$^{31}$P-NMR(161 MHz): δ-4.18 ppm.

$^{13}$C-NMR(101 MHz): δ 53.61, 54.48, 101.73 (J=27.8 Hz), 106.52 (J=2.1 Hz), 128.76 (J=7.6 Hz), 129.38, 134.07, 134.27, 134.33, 134.43, 154.13 (J=16.0 Hz), 158.62 (J=5.6 Hz), 161.5.

mass spectrum (high resolution): M.W.=401.0, consistent with C$_{19}$H$_{17}$NPBrO$_2$, melting point: 149.7°~150.8° C.

EXAMPLE 2

Preparation of 2,6-dimethoxy-3-bromo-4-(diphenylphosphinoyl)pyridine

A round bottom flask with a magnetic stirring bar was charged with 2,6-dimethoxy-3-bromo-4-(diphenylphosphino)pyridine (4.96 g) and 50 mL acetone. To this solution was slowly added approximately 35% hydrogen peroxide (33.9 mL). The reaction was monitored by thin-layer chromatography. The product was extracted with 3×20 mL dichloromethane. The combined extract was dried with anhydrous magnesium sulfate and was concentrated in vaccuo to give a crude product which was purified by column chromatography (silica gel, CHCl$_3$: ethyl acetate=1:1 with 5% NEt$_3$) to give 5.15 g pure product (96% of theoretical yield).

$^1$H-NMR(400 MHz): δ 3.90 (s, 3H, OCH$_3$), 4.01 (s, 3H, OCH$_3$), 6.30 (d, J=13.2 Hz, 1H, PyH's), 7.51~7.47 (m, 4H, PhH's), 7.58~7.56 (m, 2H, PhH's), 7.74~7.69 (m, 4H, PhH's).

$^{31}$P-NMR(161 MHz): δ 30.78 ppm.

$^{13}$C-NMR(101 MHz): δ 53.94, 54.78, 98.62 (J=4.6 Hz), 108.12 (J=11.1 Hz), 128.59 (J=12.7 Hz), 130.01, 131.08, 131.82 (J=11.1 Hz), 132.22 (J=2.0), 145.61, 146.58, 159.77 (J=12.2 Hz), 161.65 (J=16.7 Hz).

mass spectrum (low resolution): M.W.=419 (FAB), consistent with C$_{19}$H$_{17}$BrNO$_3$P melting point: 149.7°~150.7° C.

EXAMPLE 3

Preparation of 2,2',6,6'-tetramethoxy-4,4'-diphenylphosphinoyl-3,3'-bipyridine

A mixture of 2,6-dimethoxy-3-bromo-4-(diphenylphosphinoyl)pyridine (4.96 g, 11.87 mmol), copper powder (2.26 g, 35.60 mmol) and DMF (30 mL) was stirred at 140° C. for 3 hours. The mixture was evaporated to dryness with a rotary evaporator at 70° C. The residue was treated for a few minutes with hot chloroform (30 mL), the insoluble solid was removed by filtration and washed with hot chloroform (150 mL), and the combined filtrate was dried with anhydrous magnesium sulfate and the solvent was evaporated. The solid residue was washed with ethyl acetate (30 mL) to give 6.42 g of pure white powder (80% theoretical yield).

$^1$H-NMR(400 MHz): δ 3.33 (s, 6H, OCH$_3$), 3.84 (s, 6H, OCH$_3$), 6.13 (d, J$_{PH}$=13.5 Hz, 2H), 7.29~7.31 (m, 4H, PhH's), 7.44~7.46 (m, 6H, PhH's), 7.50~7.57 (m, 6H,PhH's), 7.68~7.72 (m, 4H, PhH's).

$^{13}$C-NMR(101 MHz): δ 53.01, 53.39, 104.94 (J=13.1 Hz), 113.13 (J=3.9 Hz), 113.20 (J=4.0 Hz), 128.03 (J=2.7 Hz), 128.16 (J=2.9 Hz), 131.35 (J=2.7 Hz), 131.39 (J=2.8 Hz), 132.02 (J=9.6 Hz), 132.24 (J=10.3 Hz), 133.08 (J=9.2 Hz), 134.17, 143.69, 144.66, 161.00 (J=15.4 Hz), 161.34 (J=18.9 Hz).

mass spectrum (low resolution): M.W.=676, consistent with C$_{38}$H$_{34}$N$_2$O$_6$P$_2$ melting point: 315.0°~316.0° C. (decomposed).

EXAMPLE 4

Separation of the enantiomers of 2,2',6,6'-tetramethoxy-4,4'-diphenylphosphinoyl-3,3'-bipyridine by HPLC The enantiomers of 2,2',6,6'-tetramethoxy-4,4'-diphenylphosphinoyl-3,3'-bipyridine were separated by HPLC with a DAICEL AD column (Sumika Chemical Analysis Service, Ltd.) (25 mm×250 mm). The compounds were eluted with a solvent system (isopropanol: hexane= 20:80) with a flow rate of 3.0 mL per minute. The retention time of the (R)-form isomer was at 12.24 minute and that of (S)-form isomer was at 25.06 minute.

EXAMPLE 5

Preparation of (R)-2,2',6,6'-tetramethoxy-4,4'-diphenylphosphino-3,3'-bipyridine A 100 mL, two-necked flask fitted with a magnetic stirring bar and a reflux condenser was charged with (R)-2,2',6,6'-tetramethoxy-4,4'-diphenylphosphinoyl-3,3'-bipyridine (1.00 g, 1.50 mmol) and the system was flushed with nitrogen gas. Under the nitrogen atmosphere, degassed dry toluene (50 mL), triethylamine (2.00 mL, 15.00 mmol) and trichlorosilane (1.50 mL, 15.00 mmol) were added to the flask by means of syringes. The mixture was stirred and heated at 120° C. overnight under a nitrogen atmosphere. After the solution was cooled to room temperature, 30 mL of a 10% aqueous sodium hydroxide solution was carefully added. The mixture was then stirred at 80° C. until the organic and aqueous layers became clear. The organic product was extracted with 3×20 mL portions of toluene under a nitrogen atmosphere and the extract was dried over anhydrous magnesium sulfate. The organic layer was concentrated under reduced pressure to give a crude product which was washed with cold degassed methanol to give 0.95 g of pure white powdery product (99% theoretical yield).

$^1$H-NMR(400 MHz): $\delta$ 3.30 (s, 6H, OCH$_3$), 3.81 (s, 6H, OCH$_3$), 6.02 (d, J$_{PH}$=1.2 Hz, 2H, PyH's), 7.18 (d, J$_{HH}$=3.3 Hz, 4H, PhH's), 7.31~7.26 (m, 16H, PhH's).

$^{13}$C-NMR(101 MHz): $\delta$ 52.92, 53.28, 105.05, 114.42, 114.60, 114.78, 128.03, 128.06, 128.10, 128.22, 128.35, 128.38, 128.43, 128.64, 133.40, 133.50, 133.60, 134.36, 134.47, 134.58, 135.13, 135.18, 135.23, 136.71.136.78, 136.85, 154.02, 154.08, 154.14, 160.61, 160.67, 160.73, 162.28

$^{31}$P-NMR(161 MHz): $\delta$-12.18 ppm.

mass spectrum (high resolution): M.W.=644.2, consistent with C$_{38}$H$_{34}$N$_2$O$_4$P$_2$ [$\alpha$]$^D$=+36.4° (C=1.1 in CH$_2$Cl$_2$).

EXAMPLE 6

Preparation of Ru[(cymene)(PP)Cl]Cl

To a mixture of (R)-2,2',6,6'-tetramethoxy-4,4'-diphenylphosphino-3,3'-bipyridine (46.5 mg, 0.072 mmol) and [Ru(cymene)Cl$_2$]$_2$ (21.5 mg, 0.035 mmol) in a Schlenk tube was added ethanol (5 mL) and dichloromethane (1 mL). The mixture was stirred at 50° C. for one hour and then was filtered through a celite pad. The resulting orange yellow solution was concentrated under reduced pressure to afford 32.4 mg catalyst (97% theoretical yield).

$^{31}$P-NMR(161 MHz): $\delta$ 27.35 (d, J=61.7 Hz), 41.6 (d, J=61.3 Hz).

EXAMPLE 7

Preparation of Ru(acac)$_2$(PP)

A 50 mL two-necked flask was charged with Ru(acac)$_3$ (125 mg, 0.31 mmol), (R)-2,2',6,6'-tetramethoxy-4,4'-diphenylphosphino-3,3'-bipyridine (200 mg, 0.31 mmol), zinc dust (201 mg) and degassed ethanol (5 mL) under an atmosphere of nitrogen gas. The mixture was heated to reflux overnight and followed by filtration through a celite pad. The resulting brownish yellow solution was concentrated under reduced pressure to give 284.07 mg of brownish yellow solid (97% theoretical yield).

$^{31}$P-NMR(161 MHz); $\delta$ 56.64, 57.05 ppm.

EXAMPLE 8

This example illustrates the effect of solvent on the rate and enantioselectivity of the [Ru(cymene)(PP)Cl]Cl catalyzed asymmetric hydrogenation leading to naproxen.

A glass-lined stainless steel autoclave reactor was charged with 5.00 mg of 2-(6'-methoxy-2'-naphthyl)propenoic acid, 0.10 mg [Ru(cymene)(PP)Cl]Cl and 2.50 mL of solvent. The solution was stirred well with a magnetic stirrer for 6~18 hours. Typical results are summarized in Table 1.

TABLE 1

The Effect of Solvent on the Hydrogenation of 2-(6'-methoxy-2'-naphthyl)propenoic acid

| entry[a] | solvent | reaction time (hrs) | conv.(%)[b] | e.e.(%)[b] |
|---|---|---|---|---|
| 1 | acetone | 15 | 0 | — |
| 2 | acetonitrile | 18 | 0 | — |
| 3 | chloroform | 15 | 1.4 | — |
| 4 | diethyl ether | 18 | 100 | 69.5 |
| 5 | THF | 15 | 91.6 | 70.7 |
| 6 | i-PrOH | 18 | 80.8 | 75.0 |
| 7 | EtOH | 15 | 53.6 | 77.6 |
| 8 | CH$_3$OH | 6 | 100 | 87.0 |

[a]H$_2$ pressure = 6896 KPa; substrate/catalyst = 200 (molar ratio); concentration of substrate 2.0 mg/mL, ambient temperature.
[b]The conversion and enantiomeric excess were determinated by HPLC analysis with a SUMICHIRAL OA-2500 column (Sumika Chemical Analytical Service, Ltd.).

EXAMPLE 9

This example illustrates the effect of reaction pressure on the enantiomeric excess of desired product (naproxen) by using Ru(acac)$_2$(PP) as catalyst.

A glass-lined stainless steel reactor was charged with 5.00 mg of 2-(6'methoxy-2'-naphthyl)propenoic acid, 0.10 mg Ru(acac)$_2$(PP) and 2.50 mL of methanol. The solution was stirred well with a magnetic stirrer at a chosen hydrogen pressure for 10 hours. Typical results are summarized in Table 2. It was noted that higher hydrogen pressure gave higher enantiomeric excess for the naproxen product.

TABLE 2

The Effect of Hydrogen Pressure on the Hydrogenation of 2-(6'-methoxy-2'-naphthyl)propenoic acid

| entry[a] | P(KPa) | e.e.(%)[b] |
|---|---|---|
| 1 | 3448 | 86.8 |
| 2 | 5172 | 88.7 |
| 3 | 5896 | 91.5 |
| 4 | 8276 | 91.9 |

[a]substrate catalyst = 200 (molar ratio); concentration of substract = 2.0 mg/mL; ambient temperature; complete conversion (100%) in all cases.
[b]The enantiomeric excess was determinated by HPLC analysis with a SUMICHIRAL OA-2500 column (Sumika Chemical Analytical Service, Ltd.).

EXAMPLE 10

This example illustrates the effect of the addition of an acid to the catalyst system on the enantiomeric excess in the hydrogenation of 2-(6'-methoxy-2'napthyl)propenoic acid.

A glass-lined stainless steel reactor was charged with 5.00 mg of 2-(6'-methoxy-2'-naphthyl)propenoic acid, 0.10 mg Ru(acac)$_2$(PP), 2.50 mL of methanol and a certain amount of phosphoric acid. The solution was stirred well with a magnetic stirrer at ambient temperature. Typical results are shown in Table 3.

TABLE 3

The Effect of phosphoric acid on the Hydrogenation of 2-(6'-methoxy-2'-naphthyl)propenoic acid

| entry[a] | H$_3$PO$_4$/sub. (mole %) | e.e.(%)[b] |
|---|---|---|
| 1 | 0 | 91.5 |
| 2 | 0.2 | 91.6 |
| 3 | 0.4 | 92.7 |
| 4 | 0.6 | 93.6 |
| 5 | 0.8 | 93.0 |
| 6 | 1.0 | 92.7 |

[a]H$_2$ pressure = 6896 KPa; substrate/catalyst = 200 (molar ratio); concentration of substrate = 2.0 mg/mL; 13 hours; ambient temperature; 2.5 mL of MeOH; complete conversion (100%) in all case.
[b]The enantiomeric excess was determined by HPLC analysis with a SUMICHIRAL OA-2500 column (Sumika Chemical Analytical Service, Ltd.).

It was found that a suitable amount of phosphoric acid (0.5~0.6 equivalent to 2-(6'-methoxy-2'-naphthyl)propenoic acid) increased the enantiomeric excess of product and made the system commerically more attractive. On a side-by-side comparison study, the hydrogenation of 2-(6'-methoxy-2'-naphthyl)propenoic acid with the well known Ru(BINAP)(OAc)$_2$ catalyst under 6896 KPa hydrogen and at ambient temperature gave only 89% e.e. The results in this example clearly demonstrated the advantage of this new class of chiral ligands and catalysts.

EXAMPLE 11

This example illustrates the effect of reaction temperature on the enantiomeric excess of the desired product (naproxen) by using Ru(acac)$_2$(PP) as catalyst.

A glass-lined stainless steel reactor was charged with 0.02 g of 2-(6'-methoxy-2'-naphthyl)propenoic acid, 0.10 mg Ru(acac)$_2$(PP) and 2.00 mL of methanol. The solution was pressurized with 6896 KPa H$_2$ and was stirred well with a magnetic stirrer at a fixed temperature. Typical results are summarized in Table 4. It was noted that lower reaction temperature gave higher enantiomeric excess for the naproxen product.

TABLE 4

The Effect of Reaction Temperature on the Hydrogenation of 2-(6'-methoxy-2'-naphthyl)propenoic acid

| entry[a] | H$_3$PO$_4$/sub. (mol %) | T (°C.) | e.e. (%)[b] |
|---|---|---|---|
| 1 | 0 | 25 | 91.5 |
| 2 | 0 | 0 | 95.3 |
| 3 | 0.6 | 25 | 93.6 |
| 4 | 0.6 | 0 | 96.2 |
| 5 | 0.5 | 0 | 95.5 |

[a]H$_2$ pressure = 6896 KPa; substrate/catalyst 800 (molar ratio); concentration of substract = 10.0 mg/mL; 18 hours; 2.0 mL of MeOH; complete conversion (100%) in all cases.
[b]The enantiomeac excess was determinated by HPLC analysis with a SUMICHIRAL OA-2500 column (Sumika Chemical Analytical Service, Ltd.).

EXAMPLE 12

This example illustrates the convenient recycling of the new catalyst.

A stainless steel reactor was charged with a pre-mixed solution of [Ru(acac)$_2$(PP)] (6.46×10$^{-2}$ mg, 6.85×10$^{-5}$ mmol), 2-(6'-methoxy-2'-naphthyl)propenoic acid (12.5 mg, 5.48×10$^{-2}$ mmol) and MeOH (1.00 mL). (The solution had been exposed to visible light for 24 hours before use.) The autoclave was pressurized with 6896 KPa hydrogen and stirred well with a magnetic stirrer at ambient temperature. After 30 minutes of reaction, the gas was vented and the solution was concentrated under reduced pressure. The enantiomeric excess and conversion yield of product were determined by HPLC analysis with a SUMICHIRAL OA-2500 column (Sumika Chemical Analytical Service, Ltd.) (e.e=91.6%, conversion yield=100%).

The solution containing the product was mixed with ethyl acetate (3.00 mL) and was extracted with 9N sulfuric acid solution (0.50 mL×2). The aqueous layer was poured into a Schlenk flask. Saturated aqueous sodium carbonate solution was added to neutralize the acidic solution to pH=7 under rapid stirring at 5° C. The solution was successively extracted with toluene (3.00 mL×2) and the toluene layer was separated and the ruthenium content was measured by atomic absorption spectrometry (96% of the starting ruthenium was found to be in this recycled solution) toluene solution was then concentrated to dryness under reduced pressure. The residue was dissolved in methanol (1 mL) and filtered through a celite-pad into a Schlenk flask. The recycled catalyst solution was used to repeated the hydrogenation of 2-(6'-methoxy-2'-naphthyl)propenoic acid (12.5 mg, 5.48×10$^{-2}$ mmol) following the previous procedure. The catalyst activity and enantioselectivity was found to be similar to those of the freshly prepared catalyst. The enantiomeric excess and conversion yield of naproxen was determined again by HPLC analysis with a SUMICHIRAL OA-2500 column (e.e=91.6%, conversion yield=100%).

We claim:

1. A chiral pyridylphosphine having the following formula (1):

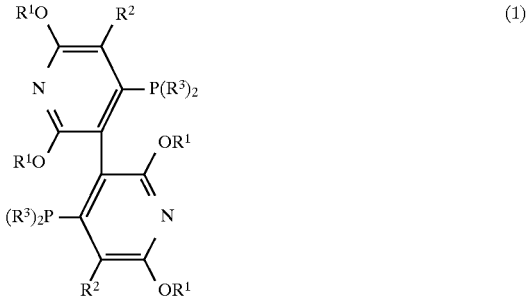

wherein:
(a) R$^1$ represents a hydrogen atom or a straight or branched-chain alkyl group having from 1 to 6 carbon atoms;
(b) R$^2$ is chosen from the following group:
   hydrogen atoms;
   halogen atoms;
   straight or branched-chain alkyl groups having 1 to 6 carbon atoms;
   straight or branched-chain alkoxy groups having from 1 to 6 carbon atoms;

hydroxy group;

straight or branched-chain chiral hydroxyalkyl groups having from 1 to 6 carbon atoms;

amino groups;

mono- and di-alkylamino groups in which the alkyl group has from 1 to 6 carbon atoms;

vinyl groups; and allyl groups; and (c) $R^3$ is chosen from the following groups:

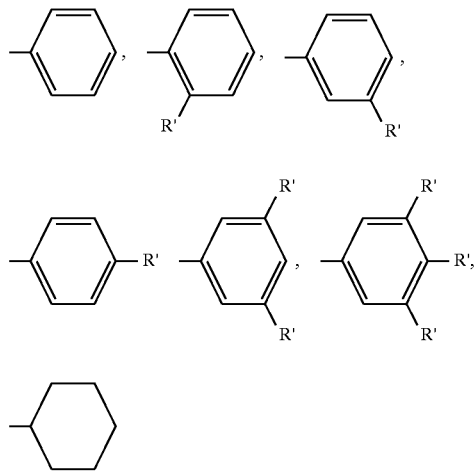

in which R' represents a straight or branched chain alkyl group having from 1 to 6 carbon atoms, a straight or branched-chain alkoxy group having from 1 to 6 carbon atoms or an amino group and, where there is more than one group R', each R' may be the same or different from the others; or the group $P(R^3)_2$ may form a group chosen from the following:

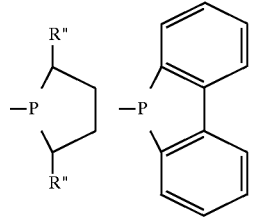

in which R" is a straight or branched-chain alkyl group having from 1 to 6 carbon atoms.

2. The chiral pyridylphosphine of claim 1 wherein formula (1) comprises 2,2',6,6'-tetramethoxy-4,4'-diphenylphosphino-3,3-bipyridine.

3. The chiral pyridylphosphine of claim 2, wherein the chiral pyridylphosphine is in (S) form.

4. The chiral pyridylphosphine of claim 2, wherein the chiral pyridylphosphine is in (R) form.

5. A process for the preparation of the formula (1) as defined in claim 1, comprising reducing a compound of formula (3), as defined below, using a silane compound:

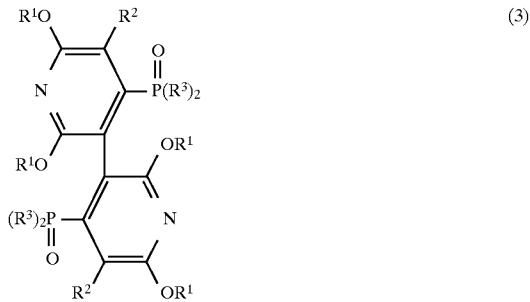

(3)

wherein $R^1$, $R^2$ and $R^3$ are previously defined.

6. The process according to claim 5, wherein the silane is trichlorosilane and reducing is carried out in an aromatic hydrocarbon solvent in the presence of an organic base.

* * * * *